US009028775B2

(12) United States Patent
Hering et al.

(10) Patent No.: US 9,028,775 B2
(45) Date of Patent: May 12, 2015

(54) GROWTH TUBE MICROCHIP ELECTROPHORESIS SYSTEM FOR MONITORING OF AEROSOL COMPOSITION

(75) Inventors: Susanne Vera Hering, Berkeley, CA (US); Gregory Stephen Lewis, Berkeley, CA (US); Steven Russel Spielman, Oakland, CA (US); Charles Sherman Henry, Fort Collins, CO (US); Scott Douglas Noblitt, Fort Collins, CO (US); Jeffrey Lee Collett, Jr., Fort Collins, CO (US)

(73) Assignees: Aerosol Dynamics Inc., Berkeley, CA (US); Colorado State University Research, Fort Collins, CO (US)

( * ) Notice: Subject to any disclaimer, the term of this patent is extended or adjusted under 35 U.S.C. 154(b) by 654 days.

(21) Appl. No.: 13/246,608

(22) Filed: Sep. 27, 2011

(65) Prior Publication Data

US 2012/0255861 A1 Oct. 11, 2012

Related U.S. Application Data

(60) Provisional application No. 61/404,098, filed on Sep. 27, 2010.

(51) Int. Cl.

| | |
|---|---|
| *B01L 5/00* | (2006.01) |
| *G01N 27/453* | (2006.01) |
| *G01N 35/08* | (2006.01) |
| *G01N 1/22* | (2006.01) |
| *G01N 27/447* | (2006.01) |

(52) U.S. Cl.

CPC .............. *G01N 35/08* (2013.01); *G01N 1/2208* (2013.01); *G01N 2001/2223* (2013.01); *G01N 27/44743* (2013.01); *G01N 27/44791* (2013.01)

(58) Field of Classification Search

CPC .................... B01L 3/502707; B01L 3/502723; G01N 30/04; G01N 30/08; G01N 27/44743

See application file for complete search history.

(56) References Cited

U.S. PATENT DOCUMENTS

| | | | | |
|---|---|---|---|---|
| 6,143,152 | A * | 11/2000 | Simpson et al. | 204/451 |
| 7,029,921 | B2 * | 4/2006 | Lee et al. | 436/148 |
| 8,398,839 | B1 * | 3/2013 | Morales et al. | 204/547 |
| 2010/0186524 | A1 * | 7/2010 | Ariessohn et al. | 73/863.22 |

OTHER PUBLICATIONS

Abstract of "Continuous Monitoring of Nitrate and Sulfate in Aerosols with Microchip Electrophoresis" given at the American Geophysical Union Fall Meeting 2007, abstract #A33B-1192, publication date Dec. 2007, downloaded on May 8, 2014 from http://adsabs.harvard.edu/abs/2007AGUFM.A33B1192N.*

(Continued)

*Primary Examiner* — Alexander Noguerola
(74) *Attorney, Agent, or Firm* — Vierra Magen Marcus LLP

(57) ABSTRACT

This technology is a method and apparatus for the semi-continuous measurement of the concentration of constituents of airborne particles which couples a laminar flow, water condensation particle collector to a microfluidic device for assay of particle chemical composition by electrophoresis. The technology has been used for the assay of sulfates, nitrates, chlorides, and organic acids contained in fine and submicrometer atmospheric particles. For these compounds the apparatus and method described is capable of one-minute time resolution at concentrations at the level of micrograms of analyte species per cubic meter of air. Extension to other analytes is possible.

21 Claims, 12 Drawing Sheets

(56) References Cited

OTHER PUBLICATIONS

Noblitt et al., "Interfacing Microchip Electrophoresis to a Growth Tube Particle Collector for Semicontinuous Monitoring of Aerosol Composition," Anal. Chem., 2009, 81, 10029-10037.*
Caplus Abstract for "Rapid Aerosol Composition Monitoring Using Microchip Electrophoresis," given at the 43rd Midwest Regional Meeting of the American Chemical Society, Kearney, NE, United States, Oct. 8-11 (2008).*
Al-Horr et al., "A Continuous Analyzer for Soluble Anionic Constituents and Ammonium in Atmospheric Particulate Matter". Environmental Science & Technology, Nov. 2003, 37(24), 5711-5720.
Garcia et al., "Determination of Levoglucosan From Smoke Samples Using Microchip Capillary Electrophoresis with Pulsed Amperometric Detection", Environmental Science & Technology, Feb. 2005, 39(2), 618-623. doi: 10.1021/es0499360.
Harrison et al., "Capillary Electrophoresis and Sample Injection Systems Integrated on a Planar Glass Chip", Analytical Chemistry, Sep. 1992, vol. 64, No. 17, 1926-1932.
Hering et al., "A Laminar-Flow, Water-Based Condensation Particle Counter (WCPC)", Aerosol Science and Technology, Jan. 2005, 39(7), 659-672.
Inami et al., "Semi-Automated Bacterial Spore Detection System With Micro-Fluidic Chips for Aerosol Collection, Spore Treatment and ICAN DNA Detection", Biosensors and Bioelectronics, May 2009, 24(11), 3299-3305. doi: http://dx.doi.org/10.1016/j.bios.2009.04.025.
Khlystov et al., "The Steam-Jet Aerosol Collector. Atmospheric Environment", Apr. 1995, 29(17), 2229-2234.
Kim et al., "Integrated Particle Detection Chip for Environmental Monitoring", Lab on a Chip, Dec. 2008, 8(11), 1950-1956. doi: 10.1039/b805264f.
Liu et al., "Analysis of Anions in Ambient Aerosols by Microchip Capillary Electrophoresis", Analyst, Dec. 2006, 131(11), 1226-1231. doi: 10.1039/b608945c.
Loflund et al, "The Performance of a Gas and Aerosol Monitoring System (GAMS) for the Determination of Acidic Water Soluble Organic and Inorganic Gases and Ammonia as Well as Related Particles From the Atmosphere", Atmospheric Environment, Jun. 2001, 35(16), 2861-2869.
Noblitt et al., "Interfacing Microchip Electrophoresis to a Growth Tube Particle Collector for Semicontinuous Monitoring of Aerosol Composition", Analytical Chemistry, Nov. 2009, 81(24), 10029-10037. doi: 10.1021/ac901903m.
Noblitt et al., "High-Sensitivity Microchip Electrophoresis Determination of Inorganic Anions and Oxalate in Atmospheric Aerosols With Adjustable Selectivity and Conductivity Detection", Journal of Chromatography A, Feb. 2009, 1216(9), 1503-1510.
Orsini et al., "Refinements to the Particle-Into-Liquid Sampler (PILS) for Ground and Airborne Measurements of Water Soluble Aerosol Composition", Atmospheric Environment, Sep. 2003, 37(9-10), 1243-1259.
Peltier et al., "Fine Aerosol Bulk Composition Measured on WP-3D Research Aircraft in Vicinity of the Northeastern United States—Results From NEAQS", Atmospheric Chemistry and Physics, Feb. 2007, 7(12), 3231-3247.
Rastogi et al., "New Technique for Online Measurement of Water-Soluble Fe(II) in Atmospheric Aerosols", Environmental Science & Technology, Feb. 2009, 43(7), 2425-2430. doi: 10.1021/es8031902.
Sierau et al., "A Condensation-Growth and Impaction Method for Rapid Off-Line Chemical-Characterization of Organic Submicrometer Atmospheric Aerosol Particles", Journal of Aerosol Science, Feb. 2003, 34(2), 225-242.
Simon et al., "Continuous Automated Measurement of Gaseous Nitrous and Nitric-Acids and Particulate Nitrite and Nitrate", Environmental Science & Technology, Jun. 1995, 29(6), 1534-1541.
Simon et al., "Continuous Automated Measurement of the Soluble Fraction of Atmospheric Particulate Matter", Analytical Chemistry, Jan. 1995, 67(1), 71-78.
Stachowiak et al., "Autonomous Microfluidic Sample Preparation System for Protein Profile-Based Detection of Aerosolized Bacterial Cells and Spores", Analytical Chemistry, Jun. 2007, 79(15), 5763-5770. doi: 10.1021/ac070567z.
Ullah et al., "Versatile Gas/Particle Ion Chromatograph", Environmental Science & Technology, Apr. 2007, 40(3), 962-968.
Weber et al., "A Particle-Into-Liquid Collector for Rapid Measurement of Aerosol Bulk Chemical Composition", Aerosol Science and Technology, Sep. 2001, 35(3), 718-727.

\* cited by examiner

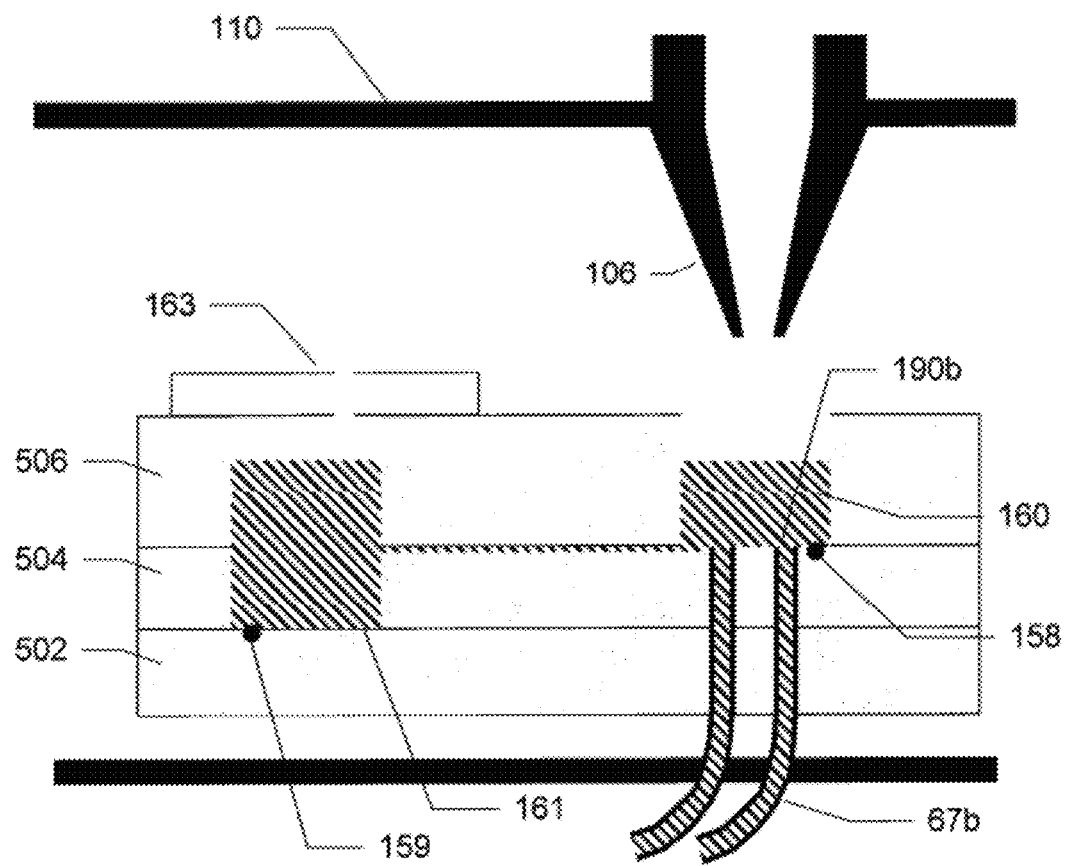

GROWTH TUBE MICROCHIP ELECTROPHORESIS SYSTEM FOR MONITORING OF AEROSOL COMPOSITION

CLAIM OF PRIORITY

This application claims the benefit of U.S. provisional patent application No. 61/404,098, filed Sep. 27, 2010, entitled "GROWTH TUBE MICROCHIP ELECTROPHORESIS SYSTEM FOR MONITORING OF AEROSOL COMPOSITION" and incorporated herein by reference.

This invention was made with government support under the following Grant Nos: U.S. Dept. of Energy STTR Phase II Grant #DE-FG02-04ER-86179; and U.S. National Science Foundation Grant #ATM-0737201 The government has certain rights in the invention.

BACKGROUND

Particulates suspended in the atmosphere originate from a wide variety of biogenic and anthropogenic sources. Water-soluble species include inorganic cations (ammonium, potassium, calcium, sodium, and magnesium), inorganic anions (sulfate, nitrate, nitrite, chloride), some heavy metals, and water-soluble organic carbon species such as oxalate, other organic acids, carbohydrates, and organic amines.

Most often these constituents are measured by in-field collection on a filter, followed by offline, laboratory-based sample extraction and analysis. Generally the time resolution is poor, and results are not known for several weeks after the collection. Inorganic ions in atmospheric particles can also be measured in-situ by coupling a steam injection particle collector to an ion chromatography analyzer.

Microchip capillary electrophoresis is an inherently less expensive and less bulky method than ion chromatography. It is more sensitive, with much lower detection limits on a mass basis. It is much faster, with separation times of the order of one minute as compared to several minutes or longer for ion chromatography. "Lab on a chip" is an established approach for the chemical analysis of solutions wherein many of the components required for the analysis are incorporated onto a microchip. Generally speaking, these microchips contain a sample reservoir that holds the solution to be analyzed, a separation channel for separating the analytes of interest from other constituents, and a means of detecting those constituents after separation. Through the application of electrical voltages or hydrodynamic forces, a small amount of solution is moved from the sample reservoir to the beginning of the separation channel. The analytes travel down the separation channel with a characteristic migration time dependent on the analyte, and are detected when they arrive at the end of the channel. The separation can be done by electrophoresis, where ions move under the influence of an electric potential difference applied across the channel. Detection can be done by measuring the change of electrical conductivity of the solution.

The prior technology requires that the solution to be analyzed be placed in the sample reservoir by pipetting or otherwise physically placing the solution into the sample reservoir.

SUMMARY

The present technology interfaces a water-based condensation growth tube collector to a microchip capillary electrophoresis device for online monitoring of aerosol chemical composition. The microchip capillary electrophoresis device, measuring a few centimeters across, contains all of the necessary components for chemical assay including sample and buffer reservoirs, separation channel and detector wires. The water condensation growth tube enables the collection of airborne particles into the sample reservoir of this microchip device. The integrated system is capable of one-minute time resolution for many inorganic ions.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIGS. 11a and 11b are enlarged cross-sections of the microchip assembled from the layers in FIG. 5 for the embodiments of FIGS. 2a and 2b, respectively.

DETAILED DESCRIPTION

The present technology couples a condensation-based airborne particle collector directly to an electrophoresis microchip to provide in-situ, time resolved analysis of chemical constituents in atmospheric particles. The present technology provides a system to deposit airborne particles, including those as small as 10 nm, directly into a buffer solution in the sample reservoir of the microchip. The soluble constituents of the deposited airborne particles dissolve in this buffer to form the solution to be analyzed. The chemical analysis by the microchip proceeds simultaneously with the process of deposition and dissolving. This simultaneous collection and analysis provides a semi-continuous measurement of the airborne concentration of soluble analytes in the airborne particles.

The present technology directly deposits airborne particles as small as 10 nm in diameter directly into the buffer-filled reservoir of a capillary electrophoresis microchip in a manner that allows direct analysis on the microchip. A unique acceleration nozzle that accommodates the competing requirements of inertial deposition and interfacial stability to allow micrometer size droplet deposition into the reservoir without disrupting the liquid surface is provided. A method for handling the hydrodynamic influence from the impinging air flow so as to allow the chemical analysis, including separation and detection to occur during sample collection, without stopping the airflow is provided. A pressure equalization means to avoid unwanted hydrodynamic flow in the channels of the microchip is utilized. The system includes flushing lines to allow the sample reservoir to be refreshed in an automated manner. These features are incorporated into a system that allows automated, semi-continuous analysis of water soluble anion concentrations in airborne particles. The embodiment described uses microchip capillary electrophoresis for the analysis of the airborne particles, but the methodology applies more generally to the interface of the condensation growth tube to analytical microchips with other analytical schemes.

Figure 1:
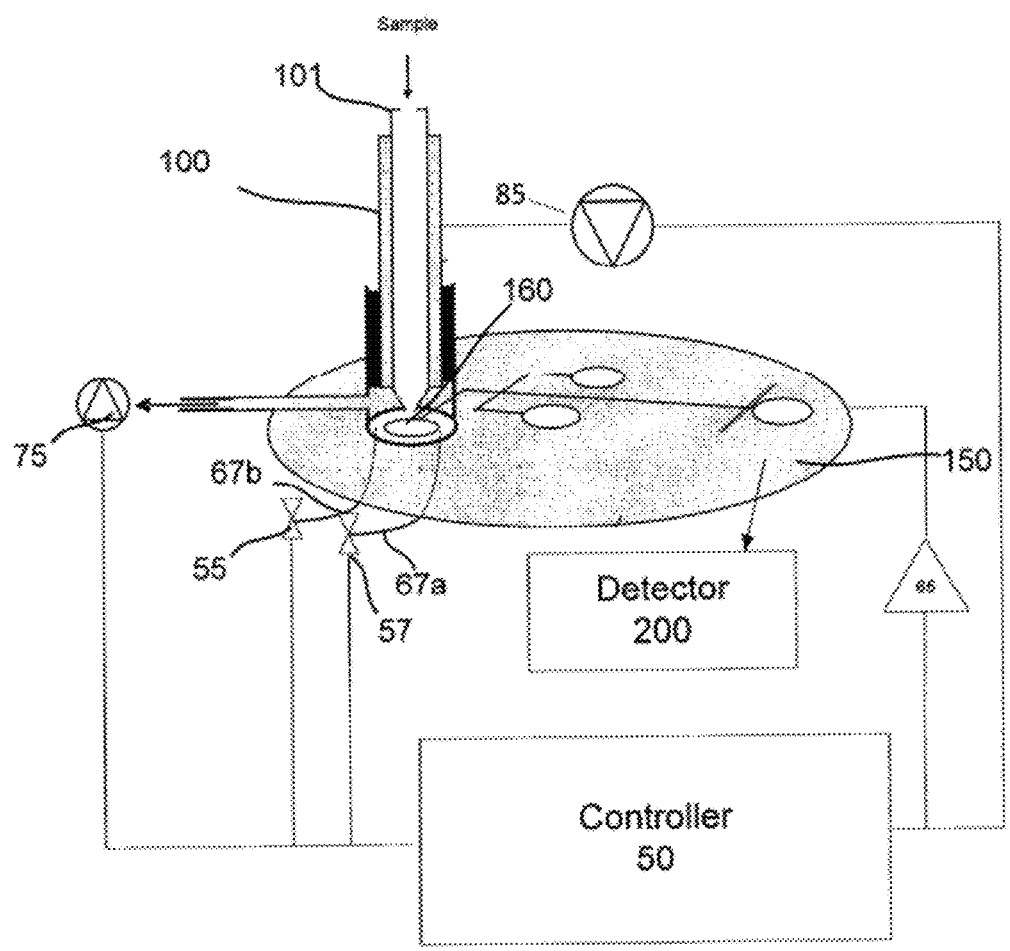
FIG. 1 is a perspective view of the system of the present technology including growth tube collector coupled to the electrophoresis microchip.

The present technology is shown in perspective view in FIG. 1. The system combines a growth tube collector 100 and an analytical microchip 150. The growth tube collector 100 enlarges airborne particles by water condensation and deposits these particles directly into a liquid filled reservoir on the microchip. The analytical microchip provides the chemical analysis of the sample. The present technology allows for direct coupling of these components to provide semi-continuous, on-chip chemical analysis of airborne particulate matter.

Figure 2A:
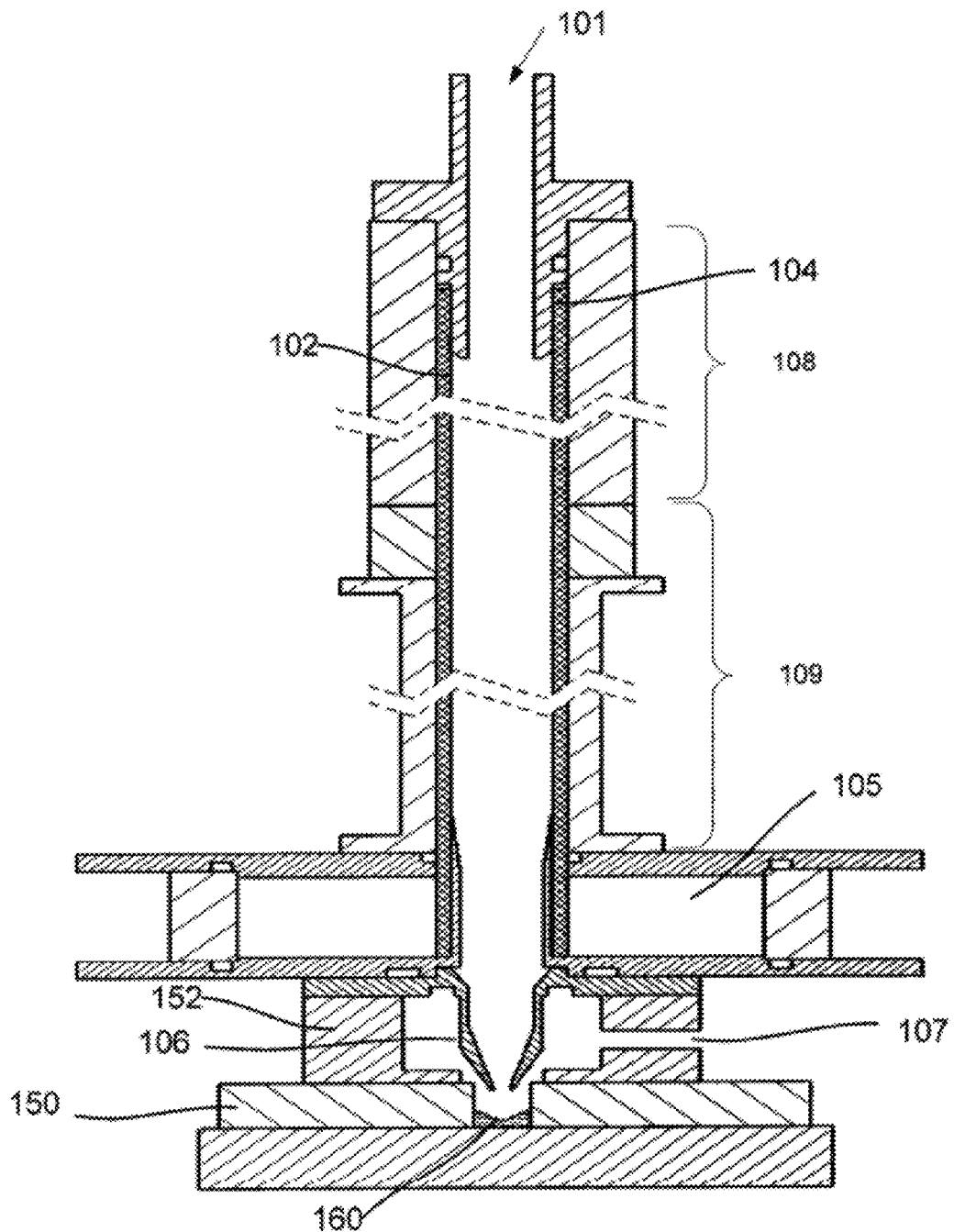
FIG. 2a is a partial cross-sectional view of the growth tube and the microchip interface of a first implementation of the technology
Figure 2B:
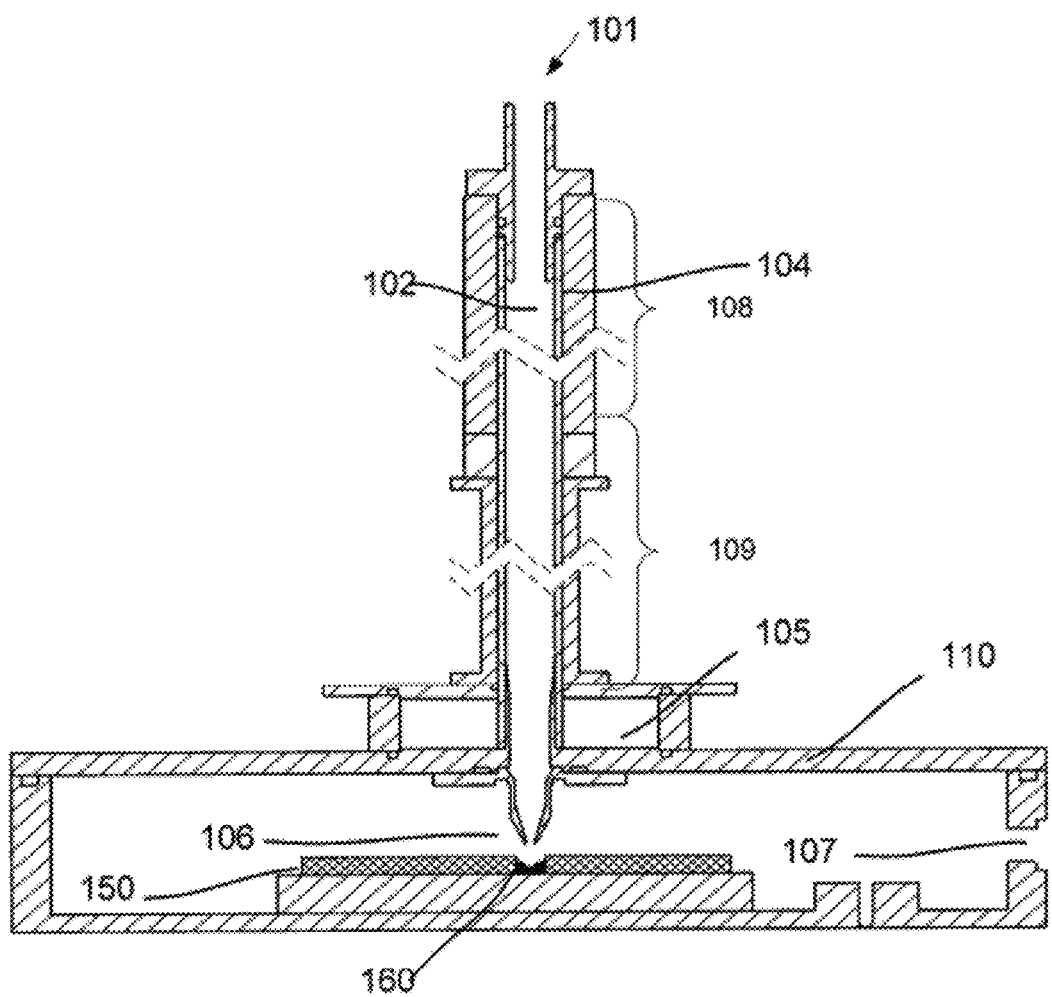
FIG. 2b is a partial cross-sectional view of the growth tube and the microchip interface of a second implementation of the technology
Figure 3:
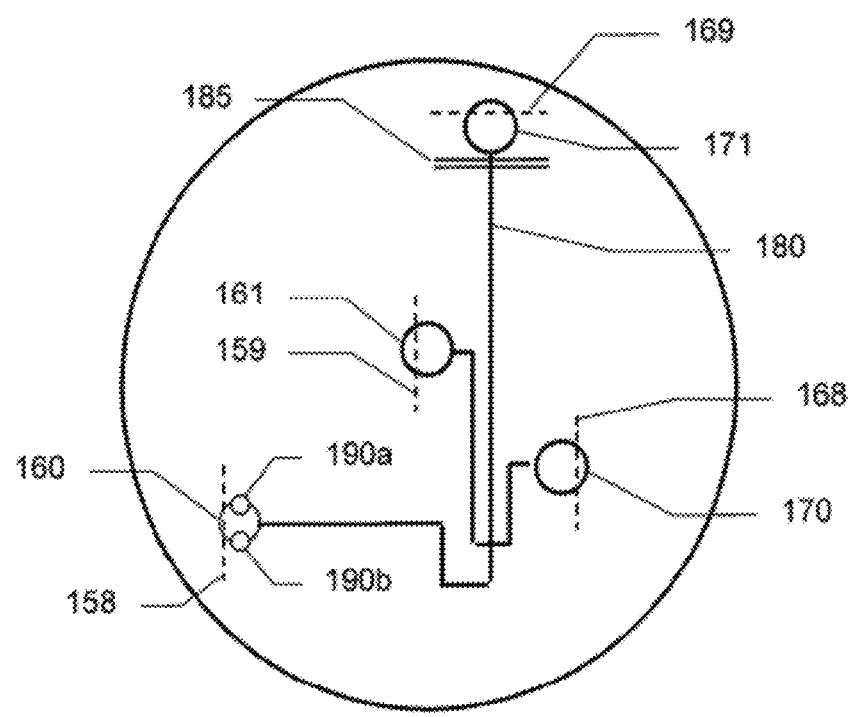
FIG. 3 is a block diagram of the analytical microchip.

With reference to FIGS. 1-3, 11a and 11b, various embodiments of the system are shown. FIG. 2a is a cross-sectional view of a first embodiment of the system. FIG. 2b is a cross-sectional view of a second embodiment of the system. FIG. 3 is a plan view illustrating components of the microchip. The growth tube collector 100 has an inlet 101 followed by a growth tube 102 and an acceleration nozzle 106. The interior walls of the growth tube are wetted by a wick material 104 in contact with a water reservoir 105. The walls of the first portion of the tube 108 are cooled, such as by a thermoelectric device. The walls of the second portion 109 are heated to provide a region of water vapor supersaturation, as described by U.S. Pat. No. 6,712,881, which is fully incorporated herein by reference.

Figure 11A:
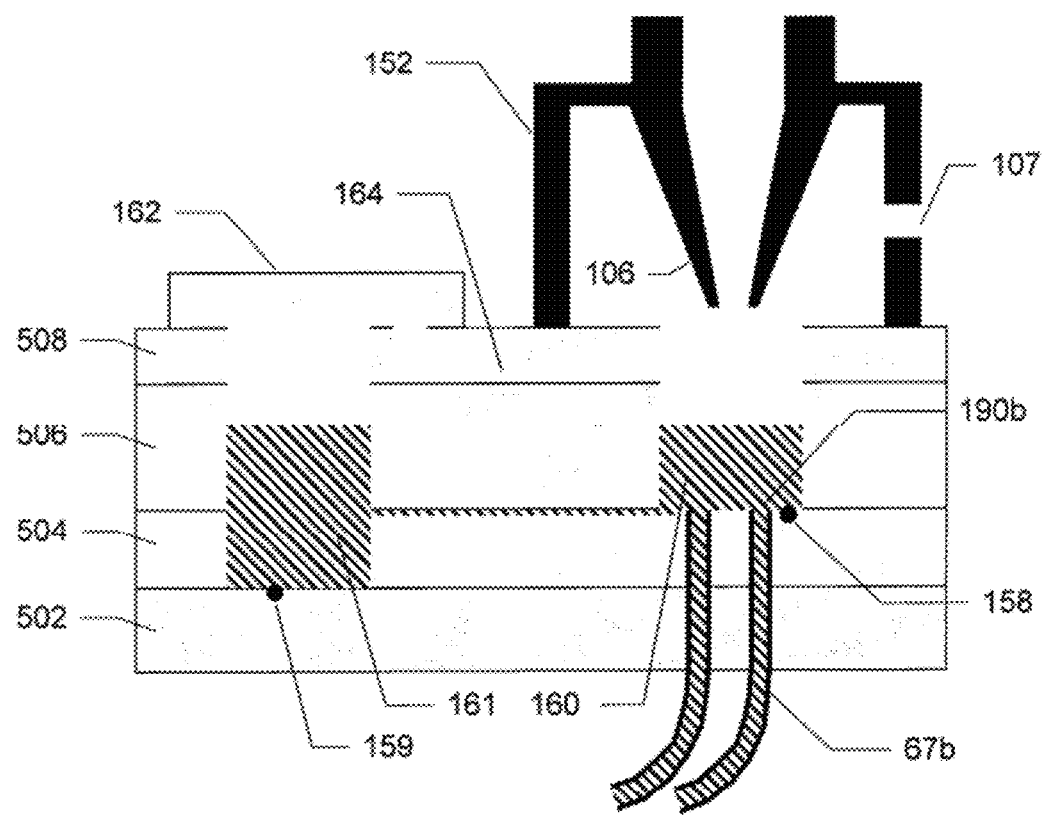

The acceleration nozzle 106 is directed towards the sample reservoir 160 located on the microchip. In the first embodiment shown in FIG. 2a the growth tube collectcor is coupled to the microchip by a housing. Detail of the junction between the nozzle of the growth tube and the microchip of this first embodiment is shown in FIG. 11a. In the second embodiment the growth tube is coupled to the microchip via a microchip chamber. FIG. 11b is a detailed view of the junction between the acceleration nozzle and the microchip for this second embodiment. The microchip contains various buffer reservoirs, a separation channel and detection electrodes or other means to detect the analytes of interest. A detector 200, for example a conductivity detector, is coupled to detection electrodes at the end of the separation channel.

The system is controlled by a controller 50 coupled to a thermoelectric device 85, voltage controller 65, and flushing pumps 55, 57. The controller also records the output of the detector 200. The operational methods described herein may be implemented by programming the controller to perform the methods discussed by operating the various devices shown herein. Controller may comprise a standard personal computer or a microchip specifically programmed to include firmware controlling the devices as discussed herein.

With reference to FIG. 3, the microchip 150 contains a sample reservoir 160 into which the airborne particles are deposited, a separation channel 180, a microchannel connecting the sample reservoir to the separation channel, a pair of embedded conductivity electrodes 185 at the end of the separation channel, a pair of flushing lines connected to the sample reservoir, and various other connecting channels, buffer and waste reservoirs. Generally the reservoirs and flow channels are filled with a buffer solution. Liquid flows are directed by application of electrical potentials between the various reservoirs.

The growth tube collector and microchip components may be coupled directly by a housing 152, as shown in FIG. 2a. These components are clamped together to form an airtight seal between the surface of the microchip 150, and the housing 152 around the nozzle 106. For operation, an air pump 75 located at the exit port 107 pulls particle-laden air from inlet 101 through the growth tube 102 and through the acceleration nozzle 106 placed at the end of the growth tube and directed towards the microchip sample reservoir 160. The air flow exits through lines 107. The growth tube 102 has two parts: the first portion 108 alternatively referred to as a preconditioner 108, followed by the second portion alternatively referred to as a condenser 109. Within the condenser 109 the flow becomes supersaturated e.g. the partial pressure of water vapor is greater than its saturation value. In this condenser region the particles suspended in the air flow are enlarged through water condensation. Most of these suspended particles are below 1 μm in diameter. As these particles pass through the water vapor supersaturation they are encapsulated into droplets of several micrometers in diameter. The airflow containing these droplets is directed through an acceleration nozzle 106 which impinges on the sample reservoir 160 of the microchip. The sample reservoir contains a small volume of buffer solution. With an appropriately designed nozzle the droplets are deposited in the solution in the sample reservoir.

FIG. 11a shows the detail of the growth tube nozzle and microchip interface for this first embodiment. Air flows from the growth tube through the acceleration nozzle 106, and impinges on the sample reservoir 160. The airflow exits out of a port 107 in the housing 152. In addition to the sample reservoir the microchip contains buffer, buffer waste and sample waste reservoirs, and a separation channel. Air ducts 164 are incorporated in the microchip and airtight lids 162 are placed on the buffer, buffer waste and sample waste reservoirs to ensure pressure balance between the sample reservoir and these other reservoirs on the microchip. In FIG. 11a only one of these other reservoirs, the sample waste reservoir, is shown, however the same air duct configuration is used to connect all four reservoirs. Electrodes within each of the reservoirs allow electrical voltages to be applied to the reservoirs. These voltages provide for electrokinetic injection of sample and for the separation of analytes within the separation channel. The microchip also has ports 190a and 190b connected to the sampler reservoir to accept the flushing lines 67a and 67b which allows the sample reservoir to be flushed and replenished from time to time. The microchip also contains a separation channel and the detector electrodes, which are not shown in FIG. 11a.

FIG. 2b shows a second embodiment of the system wherein the growth tube collector may be coupled to the microchip via a microchip chamber 110. For operation, an air pump located at the exit port 107 pulls particle-laden air from an inlet 101 through the growth tube 102 and through the acceleration nozzle 106 directed towards the microchip sample reservoir 160. The airflow exits through port 107. As described above, the particles suspended in the air stream pass through a region of water vapor supersaturation in the growth tube where they are encapsulated into droplets of several micrometers in diameter. The airflow containing these droplets is directed through an acceleration nozzle 106 and impinges onto the buffer-filled sample reservoir 160 of the microchip 150 where the particles are collected.

FIG. 11*b* is an enlargement of the interface between the acceleration nozzle and the microchip for the second embodiment. In contrast to the first embodiment shown in FIG. 11*a*, there are no air ducts incorporated in the microchip. Instead, the required pressure balance is provided by the microchip chamber 110. In this embodiment the buffer, buffer waste, and sample waste reservoirs can be covered, but the covers contain a small vent hole. These covers slow the rate of evaporation of buffer from the reservoirs, while maintaining pressure equilibrium with the microchip chamber. As in the first embodiment, this second embodiment also contains flushing lines 67*a* and 67*b*, and electrodes in each of the reservoirs. FIG. 11*b* does not show the separation channel or the detector electrodes.

One embodiment of the present technology uses a condensation growth collector 100 with a single tube, 250 mm in length, lined with a wetted wick 104 with an inner diameter of 9.5 mm. The first half of the tube is cooled by a thermoelectric device, while the second half is warmed by means of an electric heater. The growth tube wick is wetted passively by means of a water reservoir at the bottom. A standpipe in the bottom of the wick prevents gravity from carrying the water out of the reservoir into the nozzle. A pressure equalization line connects the reservoir 105 to the inlet 101, allowing the system to be operated at varying inlet pressures. The reservoir has clear walls to allow visual inspection of the water level. Generally, the growth tube was operated with the first half cooled to 2° C. and the second half warmed to around 25° C. Sample flow of around 0.7-1 L/min is drawn downward through the growth tube and a single 1.6-mm diameter plastic (nonconducting) nozzle. From there it impinges onto the surface of about 25 μL of analysis solution contained within a 4- or 6-mm diameter well 160 of the microchip. In one configuration the microchip is mounted directly against the flat-bottomed exhaust chamber housing 152 that surrounds the nozzle.

As particles are deposited in the buffer-filled sample reservoir, the soluble components dissolve and become mixed in the solution and the concentration gradually increases. The concentrations of the analytes of interest in the aqueous sample are assayed repeatedly, approximately once every minute, as described below. This analysis proceeds as the particles continue to be deposited in the reservoir, without stopping the air flow. The result is semi-continuous measure of the accumulated mass of analyte in the reservoir. Airborne concentrations are calculated from the difference in successive measures of the sample reservoir concentration.

Periodically, for example approximately once per hour, a pumping system (not shown) is employed to flush the sample collection reservoir to remove accumulated sample and to renew the buffer. The pumping system is coupled to two flushing lines 67*a* and 67*b*. One line 67*a* is an incoming line and carries new buffer solution from a buffer vial via a small pump. The second line 67*b* is an outgoing tube and pushes solution to a waste vial, again using a small pump. To flush the reservoir 160, the reservoir is successively emptied through the outgoing line 67*b* and refilled through the incoming line 67*a*. By repeating this emptying and refilling process about 4 times, the reservoir 160 is fully flushed. This flushing process provides a new start to sequential chemistry assays. The last injections prior to flushing give a cumulative concentration over the period, while the intermediate measurements can be used to see the time variation within the period.

The details of the growth tube collector can be understood in reference to FIG. 2*a*. Within the growth tube 100, air flows in a predominantly laminar fashion through a wet-walled tube, the first half of which is maintained at a colder temperature than the second half. A region of water vapor supersaturation is created in the second half of the tube as a result of the differential rate of heat and water vapor transport from warm, wetted walls, as described in U.S. Pat. No. 6,712,881. Within this supersaturated region particles grow by water condensation to form droplets a few micrometers in diameter. The supersaturation is required because the equilibrium water vapor pressure over the surface of small particles is higher than that over a similarly composed flat surface because of the energy associated with surface tension. Thus, with the exception of hygroscopic materials, particles do not readily grow through vapor condensation unless exposed to vapor supersaturation. Smaller particles have higher equilibrium vapor pressures and hence require higher supersaturation to activate condensational growth.

The size of the droplets formed by the growth tube 100 is nearly independent of the input particle size, with the result that the growth tube produces nearly uniformly sized droplets. This near-monodisperse output is a typical of condensation systems. The characteristic diameter of the droplets formed varies, depending on the system geometry, operating temperatures and the number concentration of activated particles. At low particle concentrations it is possible to form droplets above 5 μm in diameter, but the characteristic size decreases as the particle number concentration increases, regardless of system geometry. Experimental data show that at typical ambient concentrations the diameter of the droplets formed is above 3 μm. At the upper range of concentrations expected for ambient air (around $10^5/cm^3$) the final droplet size is in the range of 1.5 μm to 2 μm.

The present technology facilitates the deposition of the droplets formed within the growth tube into the water-buffer filled sample reservoir 160 of the microchip. This is done by directing air flow exiting the growth region through a nozzle 106, or set of nozzles, so that the flow impinges directly on the surface of the solution within the sample reservoir. It should be recognized that while only one nozzle is shown, multiple nozzles may be utilized. In addition, multiple sample reservoirs 160 and growth tubes 100 may be provided relative to a single microchip 150.

The flow rate and the size of the collection nozzles of the growth tube microchip interface are chosen to taking into account two factors: the inertial requirements for efficient collection of droplets formed by the condensation growth tube and the stability of the air-water interface in the presence of the impinging air jet. These can be contradictory requirements and thus the flow parameters must be carefully chosen based on the knowledge of the droplet diameter and important inertial collection and interfacial stability factors.

The inertial requirements for collection of these supermicrometer sized droplets are governed by the Stokes number, given by equation 1:

$$St = \frac{4\rho_p D_p^2 CQ}{9\pi D_{jet}^3 \eta_{air}} \quad (1)$$

Where Q is the volumetric flow through the a nozzle with diameter $D_{jet}$; $D_p$ is the particle diameter, $\rho_p$ is the particle density, C is the Cunningham slip factor, and $\eta_{air}$ is the viscosity of air ($1.81 \times 10^{-5}$ Pas). The Cunningham slip factor depends on the ratio of the carrier gas mean free path to the particle diameter, and accounts for the reduced drag in the transition from continuum to free molecular flow. When air flows through a nozzle and impinges onto a surface, particles in the flow with sufficiently large St will collide with that surface, while those with smaller St will be carried with the flow. The critical Stokes number, $St_{50}$, corresponds to the cutpoint diameter, $D_{50}$, defined as the diameter of a particle that is collected with 50% efficiency. For an airflow impinging onto a solid surface, $St_{50}$ is about 0.22. When a jet of air impinges on a water surface such that it forms a stable dimple, the critical Stokes number $St_{50}=0.25\pm0.05$, similar to that for impinging onto a solid surface. According to equation 1, attaining a cutpoint of 3 μm, as needed for operation of the growth tube under typical ambient conditions requires a value of $Q/D_{jet}^3 > 3400$ s$^{-1}$. A cutpoint of 1.5 μm, as needed for operation under high number concentration conditions, requires $Q/D_{jet}^3 > 14000$ s$^{-1}$ for efficient collection under normal atmospheric conditions.

The interface stability requirements are governed by a different dimensionless group called the Weber number. When a jet of air impinges on the surface of the water, the dimple at the water is the result of a balance between two forces. The momentum per unit time imparted by the jet is a force that expands the dimple, whereas the surface tension of the liquid works to shrink the dimple. At a sufficiently high flow rate, this stable equilibrium does not exist; the shape of the dimple changes and bubbles form. The transition from stable to unstable behavior is governed by the Weber number, a dimensionless quantity given by $$We = \frac{\rho v^2 l}{\sigma}, \quad (2)$$

where σ is the surface tension of the liquid-gas interface, v is the velocity of the fluid with density ρ—in this case, the air—and l is a characteristic length. The Weber number represents a ratio between the kinetic energy per unit volume of the air stream, $\rho v^2$, and the surface energy $\sigma/l$ required to form a bubble of diameter l.

By expressing the velocity v in terms of volumetric flow rate Q and taking the characteristic length to be the nozzle diameter $D_{jet}$, the Weber number for the system is expressed as:

$$We = \frac{16}{\pi^2} \frac{\rho_{air} Q^2}{D_{jet}^3 \sigma} \quad (3)$$

Experimentally, it has been determined that the dimple is stable and the cutoff occurs where expected (that is for value of the critical Stokes number in the range between at 0.2 to 0.3) when We≤1.5.

When the Stokes number and Weber number criteria are combined, the nozzle diameter and maximum flow are completely determined by the desired cutoff $D_{50}$ and other known quantities, as follows:

$$Q = \frac{\pi We \rho_p \sigma C D_{50}^2}{36 St \rho_{air} \eta} \quad (4)$$

$$D_{jet} = \left(\frac{We \sigma \rho_p^2 C^2 D_{50}^4}{81 St^2 \rho_{air} \eta_{air}^2}\right)^{\frac{1}{3}} \quad (5)$$

For We=1.5 and $St_{50}$=0.25, these relations reduce to: Q=0.11 $CD_{50}^2$ L min$^{-1}$ μm$^{-2}$ and $D_{jet}$=0.38$CD_{50}^{4/3}$ mm μm$^{-4/3}$. For droplets above 1 μm the slip factor C is approximately equal to 1. In this limit these expressions may also be written as $D_p^2$=9.6 Q μm$^2$minL$^{-1}$ and $D_{jet}$=1.7$Q^{2/3}$ mm L$^{-2/3}$ min$^{2/3}$. This means that with an air flow of 1 L/min through a single nozzle, it is possible to attain a cutpoint of 3 μm, while a cutpoint of 1.4 μm requires that the air flow per nozzle be reduced to 0.2 L/min. The corresponding nozzle diameters are 1.7 mm and 0.6 mm for collection cutpoints of 3 μm and 1.4 μm respectively. If a larger flow rate is desired than meets these criteria, then the flow from the growth tube can be directed into a set of multiple nozzles operating in parallel, whose flows impinge into a single sample reservoir.

Under the above described constraints of flow and jet diameter, particulate matter from the growth tube can be continuously deposited in the buffer-filled sample reservoir of the microchip. The concentrations of analytes that accumulate in this reservoir are determined through repeated injections through a microchannel leading from the sample reservoir to the separation channel. All of these analytical components are part of the microchip. The injection and analysis steps are run repeatedly, without stopping the air flow to provide a semi-continuous measure of the accumulated mass. Ambient air concentrations are determined by difference between successive measurements.

The features and operation of the microchip 150 can be understood with reference to the plan schematic view of FIG. 3. Typical overall dimensions for the microchip are 80-100 mm in diameter, or a roughly rectangular shape 60 mm×90 mm. The microchip contains the sample reservoir 160, sample waste reservoir 161, the buffer reservoir 170, and the buffer waste reservoir 171. These reservoirs are joined by narrow channels, as shown. The separation channel 180 extends from the intersection of the channels to the buffer waste reservoir. This separation channel is also referred to as the separation capillary. Typical channel dimensions are about 50 μm×40 μm, and 10-60 mm long. Generally the sample reservoir is 3-6 mm wide and 1-2 mm deep, while the buffer, buffer waste and sample waste reservoirs are as much as 30 mm wide and 6 mm deep. All channels and reservoirs are filled with an electrolyte solution, such as a phosphate, borate or and organic acid mixed in water. Voltages can be applied independently to each of the four reservoirs by means of electrodes 158, 159, 168, 169 in contact with the liquid in the reservoir to move solution and samples between the reservoirs by electro-kinetic mechanisms. The field strength in the channels combined with the chemistry of the electrolyte solution determines the overall flow rate and the sample ions that can be analyzed. Ports 190a and 190b couple to flushing lines 67a and 67b, respectively, on opposite sides of reservoir 160.

The microchip has two configurations with respect to the applied voltages. These may be referred to herein as "separation" configuration and "injection" configuration. Most of the time, (as much as 99% or more), the microchip is in the separation configuration. In one embodiment, the microchip enters injection configuration briefly once every minute or so (typically at intervals of 30-180 seconds). Each injection and the separation that follows provides a measure of the accumulated concentration of the target analyte in the sample reservoir at the time of the injection During the entire process, and during both configurations of the microchip, ambient air flow continues to be drawn through the growth tube 100 and airborne particles continue to be deposited in the sample reservoir 160.

In the separation configuration the voltages at both the sample reservoir electrode 158 and buffer reservoir electrode 168 are higher than the sample waste electrode 169 and buffer waste electrode 159, and are also higher than the voltage at the intersection of the four channels. In this configuration there is a small flow from the sample reservoir to the sample waste. Additionally, the voltage between the buffer and buffer waste reservoirs provides the electric field within the separation capillary that drives the analyte separation based on electrophoretic mobility. In the configuration used here, the electrodes at the sample and buffer reservoirs are held at a few thousand volts and those at the sample waste and buffer waste reservoirs are grounded. However, it is not the absolute values of the voltages that matter, only the potential differences between the reservoirs.

In the injection configuration the voltage at the buffer reservoir is allowed to float momentarily. This forces some of the flow from the sample reservoir into the separation channel. To stop the injection the voltages are returned to the separation configuration. Typically the time for injection is on the order of 0.1-5 seconds. The volume of sample injected into the separation channel ranges from picoliters to nanoliters depending on the injection time, electrolyte chemistry and the size of the reservoirs. While the configuration shown here depicts what is described as a "gated" injection, other injection types are employable, each with their own benefits and disadvantages. These other injection types can be used with only small configuration changes to the microchip or applied voltages. As is well known in the field, the injection can be also done using hydrodynamic (pressure differential) forces instead of, or in addition to, electro-kinetic forces.

Once the injection stops, the sample ions travel down the separation channel under the influence of the electric field. The strength of the field is determined by the potential difference between the junction and the buffer reservoir. The more mobile ions migrate most quickly and reach the buffer reservoir ahead of the less mobile species. The arrival of the ions at the detection zone immediately before the buffer waste reservoir is detected as a change in the conductivity. In this embodiment the conductivity is measured by a pair of embedded electrodes 185 positioned at the end of the separation channel, as described by U.S. Pat. No. 8,012,328, which is fully incorporated herein by reference. Other detection methods can be employed and at varying locations along the separation channel if desired. The arrival time relative to the injection is characteristic of the ion, whereas the change in conductivity is proportional to the ion concentration. The trace of the conductivity with time is referred to as an electropherogram, and exhibits a series of peaks for the various analytes. Ion concentrations can be derived from the electropherogram. Concentrations may be determined with respect to the signal of an internal standard, although this is not required. In the microchip design applied here the channel is widened slightly at the detection point to provide greater sensitivity and permit higher applied potentials for shorter analysis times. Separation times are typically less than one minute.

The sample injection and analysis cycle is repeated approximately once per minute although the exact time is dependent on the electrolyte and sample chemistry. During this time airborne particles continue to be deposited in the sample reservoir 160. In a majority of cases this addition of ions from the collected particles is higher than the depletion from the repeated injections, and the concentration of ions in the sample reservoir continues to increase. Additionally, the exact volume injected depends on the overall conductivity of the solution in the reservoir. This can shift with repeated injections, as the ions in the buffer become somewhat depleted by the multiple injections. This effect can be tracked through use of an internal standard. The standard also accounts for any dilution or concentration incurred from volume changes in the sample liquid.

In normal operation the airborne particles continue to accumulate in the sample reservoir over a period of many injection and analysis cycles. After a set period of time, the injections are temporarily halted, and the sample reservoir is emptied, flushed and refilled by means of the flushing lines 67a/67b. The flushing lines are small diameter tubes, approximately 1-2 mm OD connected directly the bottom of the sample reservoir. Their diameter is much smaller than the diameter of the sample reservoir itself. Generally these flushing lines are configured to couple to ports 190a and 190b on opposite sides of the sample reservoir bottom. This provides a new buffer and a new baseline for the concentration measurements. The flushing period is determined by a user based upon the chemistry, the instrument flow rate, and the sample volume. The sample reservoir 160 is emptied through one line, and refilled through the other line, and this step is repeated several times. Flow within the chip can be driven hydrodynamically, that is by pressure differences among reservoirs, as well as by voltages.

When applied to the measurement of the airborne concentration of ionic constituents in atmospheric particles, it is necessary to derive the airborne ion concentrations from the measured concentrations in sample reservoir and the particulate accumulation rate into the reservoir due to particle deposition. For analyte 'i', accumulation rate is equal to ambient aerosol concentration ($C_{aer}$, μg $m^{-3}$) multiplied by sampling rate ($Q_{samp}$, L $min^{-1}$) and the t (s) is collection time. The aqueous concentration ($C_{aq}$, μmol $L^{-1}$), depends on the sample volume ($V_{liq}$, μL), and the molecular mass (M, g $mol^{-1}$). For non-destructive techniques when no analyte is leaving the system the resulting accumulation rate is given by equation 6:

$$\frac{dC_{i,aq}}{dt} = \frac{50C_{i,aer}Q_{samp}}{3\ M_iV_{liq}} \tag{6}$$

In microchip electrophoresis analysis equation 6 must be corrected to account for the small portion of the sample that exits to the microfluidic network for analysis. This effect, termed ion depletions most easily understood from a mass, not concentration, analysis. The rate of material accumulation by the growth tube ($dn_{acc}/dt$, μmol $s^{-1}$) is equal to the volumetric collection rate (Q, L $min^{-1}$) multiplied by the aerosol concentration ($C_{aer}$, μg $m^{-3}$) divided by the molecular weight of the ion (M, g $mol^{-1}$). After unit conversions, equation 7 results for species 'i'.

$$\frac{dn_{acc,i}}{dt} = \frac{Q_{samp}C_{aer}}{60000\ M_i} \tag{7}$$

The rate of depletion from the reservoir is equal to the analyte's volumetric flow rate multiplied by the solution concentration, $C_{aq}$ (μmol $L^{-1}$). The volumetric flow rate is defined by the exiting velocity (v, cm s$^{-1}$) multiplied by the channel cross-sectional area (A, m$^2$). In the absence of hydrodynamic flow, the velocity is the product of the electric field (E, V cm$^{-1}$) and the sum of the ionic and electroosmoticmobilities ($\mu$ and $\mu_{EOF}$, cm$^2$ V$^{-1}$ s$^{-1}$), equation 8:

$$v = E(\mu_i + \mu_{EOF}) \tag{8}$$

Equation 8 allows the rate of the depletion (dn$_{dep}$/dt, µmol s$^{-1}$) to be written as equation 9:

$$\frac{dn_{dep}}{dt} = 10 C_{i,aq} E(\mu_i + \mu_{EOF}) A \tag{9}$$

The net change in moles of an analyte in the sample reservoir (dn/dt, µmol s$^{-1}$) is the accumulation rate minus the depletion rate, yielding equation 10:

$$\frac{dn}{dt} = \frac{C_{i,aer} Q_{samp}}{60000\, M_i} - 10 C_{i,aq} E(\mu_i + \mu_{EOF}) A \tag{10}$$

The change in moles can be converted to change in concentration by dividing by the sample solution volume (V$_{liq}$, µL). Appropriate unit conversions give equation 11:

$$\frac{dC_{i,aq}}{dt} = \frac{50 C_{i,aer} Q_{samp}}{3\, M_i V_{liq}} - \frac{10^7 C_{i,aq} E(\mu_i + \mu_{EOF}) A}{V_{liq}} \tag{11}$$

This equation is difficult to evaluate in sampling situations because C$_{aer}$, C$_{aq}$, and V$_{liq}$ all change with time, and $\mu_{EOF}$ may fluctuate. Assuming constant $\mu_{EOF}$, no hydrodynamic flow, and no evaporation or condensation, V$_{liq}$ is given by Equation 12, where V$_o$ (µL) is the initial reservoir volume.

$$V_{liq} = V_o - 10^7 E \mu_{EOF} A t \tag{12}$$

Determining C$_{aer}$ in sampled air is further complicated because electrokinetic injections are sensitive to the sample conductivity and an internal standard must be used to account for both conductivity and volume changes. A linear response is expected for the ratio of analyte to internal standard, typically using peak areas (P$_i$ and P$_{IS}$, respectively). Equation 13 describes this behavior, where F is the relative response (calibration slope) and C$_{IS}$ (µM) is the internal standard concentration.

$$C_{i,liq} = \frac{C_{IS}}{F} \frac{P_i}{P_{IS}} \tag{13}$$

In most applications, the internal standard and analyte concentrations are assumed constant at initial values. For this system, Equation 11 shows that each ion depletes at a different rate, including the internal standard, so calculated concentrations (aqueous and aerosol) increasingly deviate from actual concentrations with time. In practice, equation 6 and equation 13 are used to calculate C$_{aer}$, requiring experiments to be designed so the depletion term in Equation 11 is small to ensure an acceptable level of systematic error.

Figure 4:
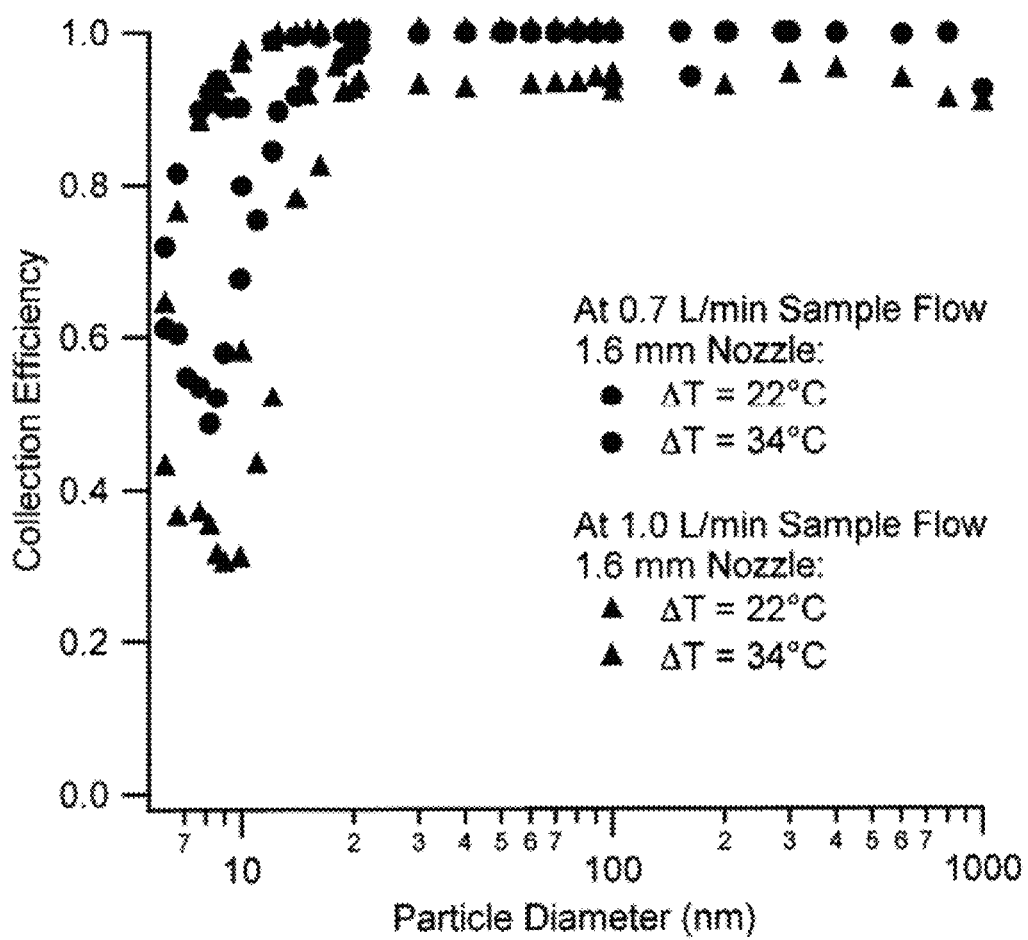
FIG. 4 is a graph of the particle size-dependent collection efficiencies for the growth tube microchip technology.

FIG. 4 is a graph showing collection efficiencies onto the microchip as a function of particle size for this embodiment. The test aerosol was composed of ammonium fluorescein (non-hygroscopic, solid particles). Data are for air sampling rates of 0.7 and 1 L min$^{-1}$, preconditioner temperature of 2° C., and condenser temperature of 24° C. and 36° C. At the 34° C. temperature differential, the lower cutpoint, defined as the size collected with 50% efficiency, is below 7 nm for both flow rates. For the smaller differential of 22° C., the lower cutpoint varies from 9 to 12 nm, depending on sampling rate. The lower flow rate provides more time for droplet growth, creating larger droplets that are more readily collected. At particle concentrations above 20000 cm$^{-3}$, the collection efficiencies decline, irrespective of particle size.

Figure 5A:
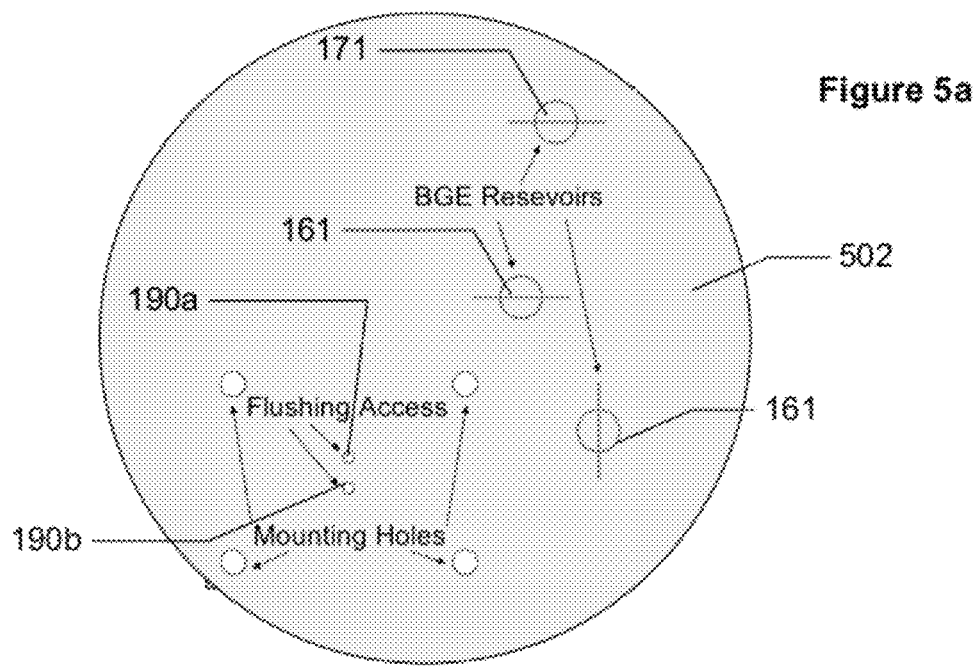
FIGS. 5a-5d are block diagrams of a plan view of each of four layers of material comprising the microchip discussed herein.
Figure 5B:
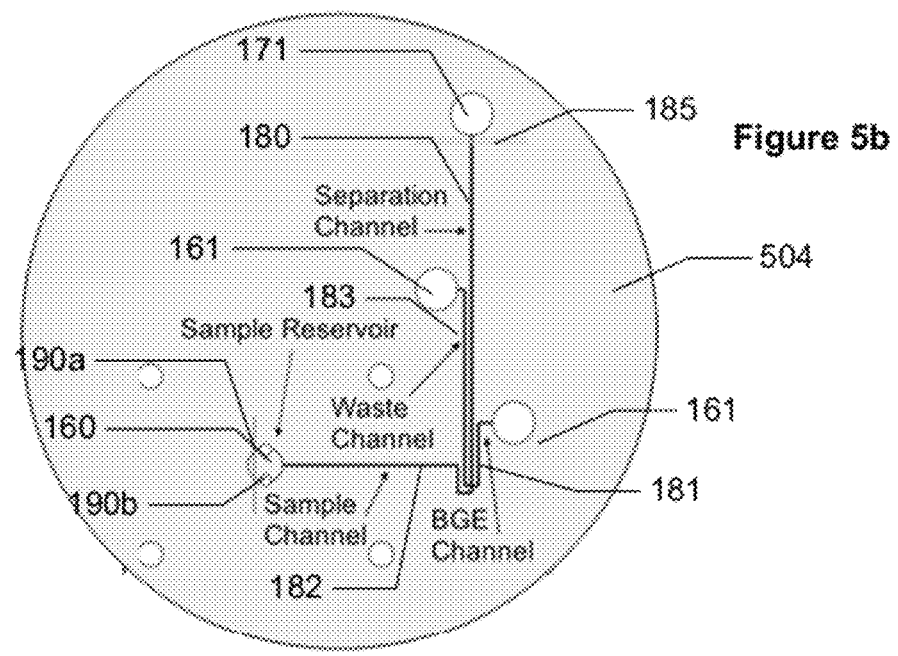
Figure 5C:
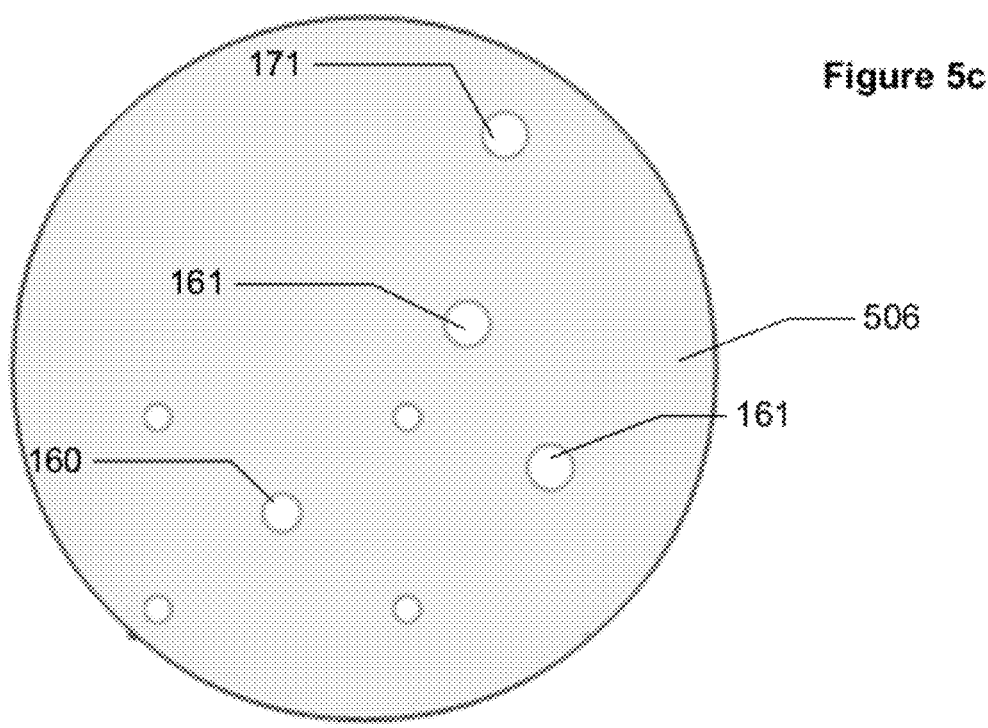
Figure 5D:
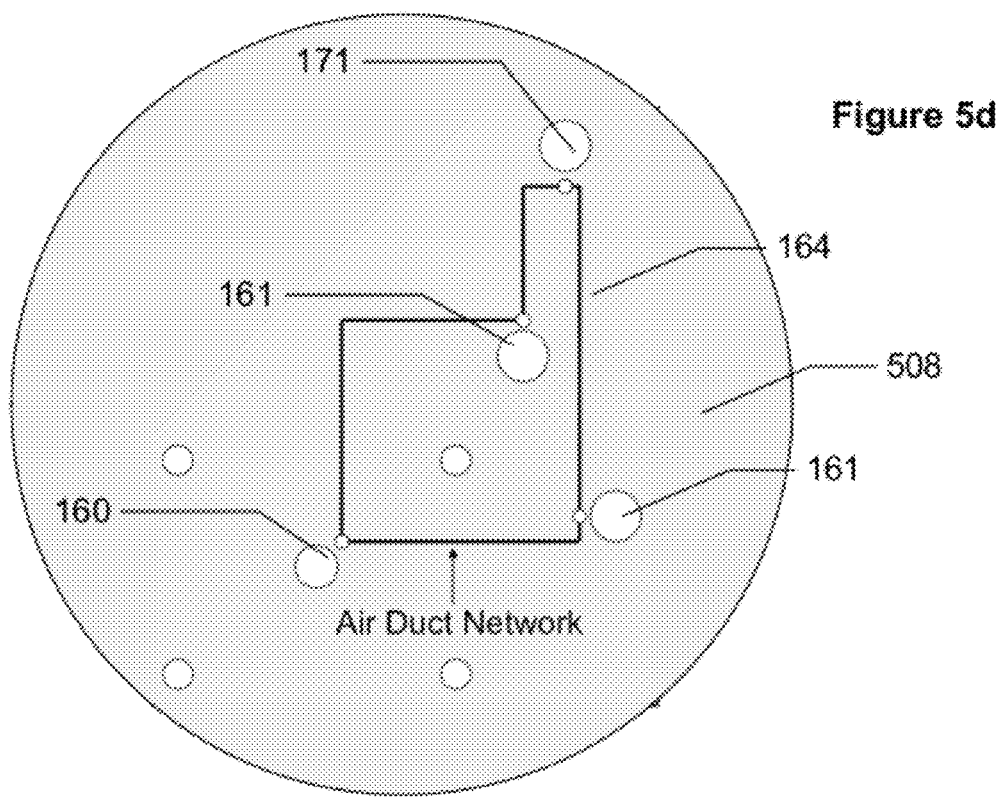

The microchip 150 used in this embodiment consists of three or four layers of polydimethylsiloxane (PDMS) layers which are combined to assemble the microchip. Each of these layers is shown in FIGS. 5a-5d, and portions of which are shown in cross-section adjacent to the outlet 106 in FIGS. 11A and 11B. FIG. 5a shows a bottom layer 502 having a thickness of ~2.3-mm and a 41-µm feature height in which background electrolyte reservoir bottoms (6-mm diameter) which are formed with each reservoir including a 25-µm platinum electrode for electrophoresis. FIG. 5b shows a second layer 504 having a ~2.5-mm thickness with 28-µm features. Features formed in layer 504 include the microfluidic channels (which may, for example, be 50-µm wide), separation channel (which may, for example, be 50-µm wide), detection electrodes 185, bottom of the sample reservoir (which may, for example, be 5-mm diameter), and a 25-µm electrode in the reservoir for electrophoresis. Two 1.5-mm diameter holes form ports 190a and 190b in the sample reservoir 160 to couple to the flushing lines. Exemplary channel lengths (in mm) are as follows: buffer=12, sample=30, waste=30, and separation=51 (50 mm effective). Detection electrodes (15-µm diameter) are composed of gold-plated tungsten. FIG. 5c illustrates a third layer 506~(2.3-mm thick) which is formed to increase reservoir volumes and separate the second 504 and fourth layers 508. The fourth layer 508 contains air ducts, and is used for the first embodiment of FIG. 2a. It is not used for the second embodiment of FIG. 2b.

As illustrated in FIGS. 11a and 11b, the interface between the microchip and the nozzle of the growth tube collector is designed to ensure equal pressures among the four reservoirs of the microchip. This is accomplished using the housing 152 or microchip chamber 110. Specific steps are taken in the interface of this technology to equalize the pressure among the reservoirs, so that the flows are controlled by the applied voltages or hydrodynamics. For the interface of FIG. 2a, illustrated in FIG. 11a) just the sample reservoir 160 is coupled to the exit of the growth tube, and this will be at the pressure of the airflow inside the growth tube, which may be different than the ambient pressure of the space surrounding the chip itself. To equalize the pressure for this configuration, a set of air venting channels 164 are constructed interior to the chip itself, as described below. Equalization of the pressures is critical to the performance, as sampling lines may come from a source that is at a different pressure than the ambient pressure where the measurement system is located.

In the direct configuration shown in FIG. 2a, a fourth layer 508 having a thickness of, for example, ~0.9-mm and 57-µm features is formed to contain 0.75-mm wide air ducts 164 that connect the four reservoirs. The air ducts 164 are joined to each reservoir by way of air-tight lids 162, as shown in FIG. 11a. The pressure at the sample reservoir is defined by the sampling conditions, so placing airtight lids over the three background electrolyte reservoirs allowed isobaric operation and minimizes interference from pressure-induced flow. Capping the reservoirs also minimizes evaporation, reducing compositional changes in the background electrolyte.

In the configuration shown in FIG. 2b, the fourth layer may be omitted. The pressure equilibration among the reservoirs is accomplished by simply placing the chip in a microchip chamber 110. As shown in FIG. 11b, lids containing a small vent hole 163, may still be placed over the three other electrolyte reservoirs. This reduces evaporation of the buffer. Pressure equalization to the interior of the box is achieved by a small vent hole in each lid.

This microchip 150 may use a bubble cell for improved conductivity detection, as described by S. D. Noblitt and C. S. Henry, C. S. (*Anal. Chem.* 2008, 80, 7624-7630), hereby fully incorporated by reference herein. The bubble cell refers to the slightly widened section in the separation channel where the electrical conductivity measurement is made. This is located at the end of the separation channel immediately before it exits to the buffer waste reservoir. In one embodiment, the detection zone bubble cell was four times the width of the separation channel (thus, 200 µm for a 50 µm separation channel), and had a ramp-up length (separation channel length from start of the bubble cell expansion to the maximum expansion width) of 375 µm. Within the detection zone, 30-µm channels (tapered to 15 µm near the separation channel) were placed perpendicularly to the separation channel. These channels terminated 40 µm before reaching the separation channel, forming a PDMS "bridge" that improved the stability of the wire location and decreased solution leakage from the separation channel. Center-to-center wire spacing was 100 µm, yielding an estimated DC potential drop of 0.75 V between electrodes at the −300 V/cm separation field present in the standard operating conditions used in this work.

In this embodiment sulfate, nitrate and oxalate separations were performed using 30 µL of a picolinic acid, N-(2-hydroxyethyl)piperazine-N'-(4-butanesulfonic acid) and 3-(N,N-dimethylmyristylammonio)propanesulfonate background electrolyte and internal standard (15-µM potassium 1,3-propanedisulfonate (PDS) as the sample and 125 µL of background electrolyte in the other reservoirs. The small sample volume was chosen to increase sensitivity during sampling, and the large background electrolyte volumes were used to combat buffer depletion during long analyses. Although some flow was induced from fluid height and Laplace pressures, effects from these were negligible because the fluid height differences were small, the Laplace pressures in each reservoir were similar because of the comparable and large reservoir radii, and hydrodynamic flow should affect the calibration and sampling analyses similarly. Separations were done using −2227 V applied to the sample and buffer reservoirs grounding the waste and separation reservoirs, providing a −300 V cm$^{-1}$ separation field. Gated injections (1.5 s) were performed by matching the buffer reservoir voltage to that calculated for the channel intersection (−859 V). Conductivity detection was done with a CD20 conductivity detector (available from Dionex, Corporation, Sunnyvale, Calif.) attached to the detection electrodes. The conductivity signal was monitored at 10-kHz with boxcar averaging set to 1000 for a 10-Hz effective rate. No additional data filtration was used. Data were baseline subtracted using a polynomial fit to the baseline to adjust for drift from ion depletion, temperature changes, and evaporation. Conductivity peaks were fit to normal distributions, providing peak height, area, and migration time.

Using this embodiment experiments were conducted to assess the validity of the depletion correction, the effectiveness of the pressure equalization approach, the efficiency of the flushing system, the comparability of on-line and off-line analysis, and the stability for continuous operation. The steps of sampling, injection, separation, detection and periodic flushing have been automated so that the system can be operated autonomously. In this mode it provides a continuous data set with one-minute resolution.

Figure 6:
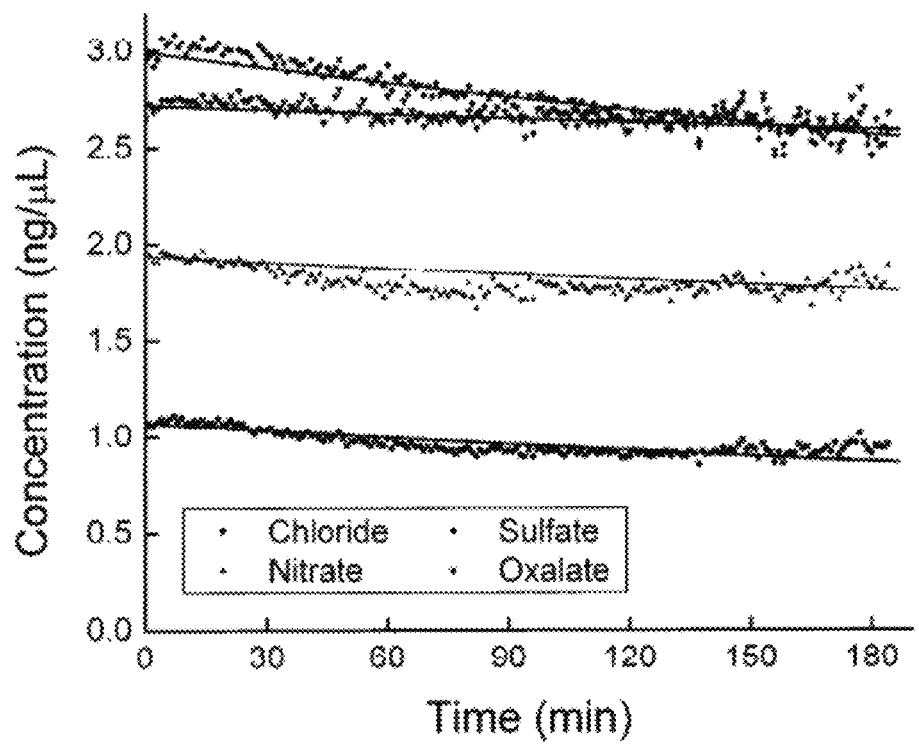
FIG. 6 is a graph showing a comparison between experimental measurements (points) of an aqueous sample analyzed for over three hours and predicted measured concentrations using depletion theory (lines).

For multi-hour monitoring, the depletion term in equation 11 is significant. The depletion model above may be used to evaluate the necessary sample regeneration interval required to avoid unacceptable error from this effect. First, the accuracy of equations 11 and 13 were evaluated through repeated analysis of a single aqueous sample over a period of ~3 h. As shown in FIG. 6, the measurements are in qualitative conformity with the calculations from the above equations. Next, having validated our depletion model, we simulated the effect of ion depletion on aerosol quantification. The largest deviations are observed for analytes that most closely match the mobility of the internal standard, which is opposite of the behavior seen in FIG. 5. This effect is rationalized by realizing that the depletion of the internal standard will affect apparent analyte concentrations uniformly, but this effect is offset by depletion of the analytes, and early-migrating ions deplete more rapidly. Consequently, any analytes migrating after the internal standard would show higher positive deviations, and if an ion with a higher mobility than chloride was analyzed, it would show increased negative deviations. It was found that systematic deviations are about +4.4% for oxalate, +2.7% for nitrate, +0.7% for sulfate, and −1.3% for chloride for 1-h sampling, and this error is acceptable for most applications.

Figure 7:
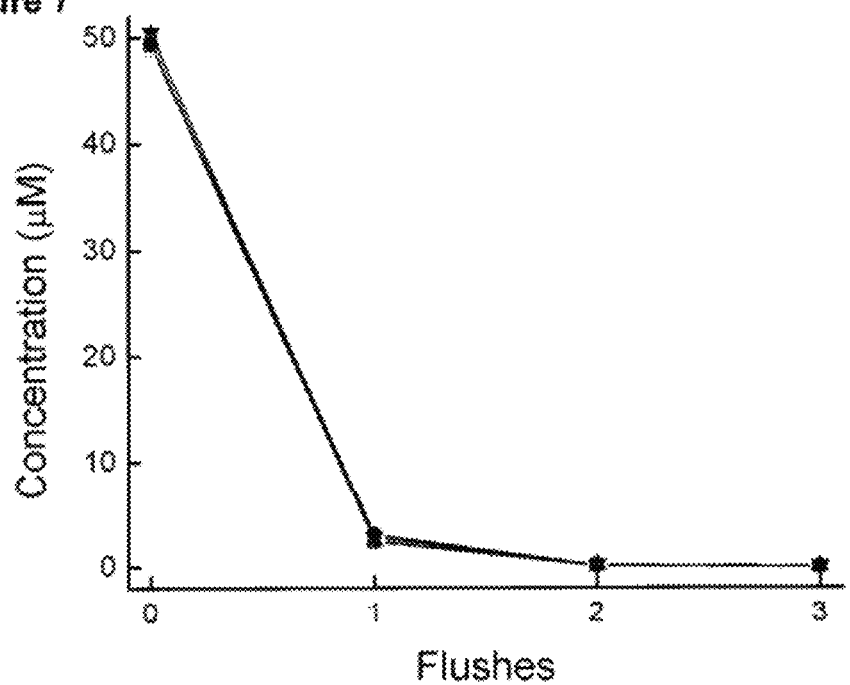
FIG. 7 shows the characterization of the sample flushing system. An aqueous sample underwent 0, 1, 2, or 3 sample flushing cycles, followed by quantitative analysis.

FIG. 7 shows the characterization of the sample flushing system. An aqueous sample underwent 0, 1, 2, or 3 sample flushing cycles, followed by quantitative analysis. Each point shown is the average of 6 independent trials (3 replicate injections per trial). Chloride (black), sulfate (red), nitrate (green), and oxalate (blue) show similar removal efficiency for each analyte (~95% per flush).

To test flushing efficiency, a sample of ~50-µM analytes was analyzed after 0-3 flushes (each performed with fresh solution to avoid depletion effects). Three consecutive flushes yielded concentrations below the LODs, as shown in FIG. 7. Calculated single-flush efficiencies were 95.3±0.4% for chloride, 93.9±0.7% for sulfate, 95.1±0.6% for nitrate, and 94.6±0.8% for oxalate (n=6 for all). For ambient analyses, a two-flush cycle was chosen because this minimizes instrument downtime (~3 min) while still achieving nearly complete flushing. Although low concentrations after two flushes make analyses less certain, respective two-flush efficiencies were 100.0±0.2%, 99.8±0.2%, 99.8±0.2%, and 99.7±0.2%

Figure 8:
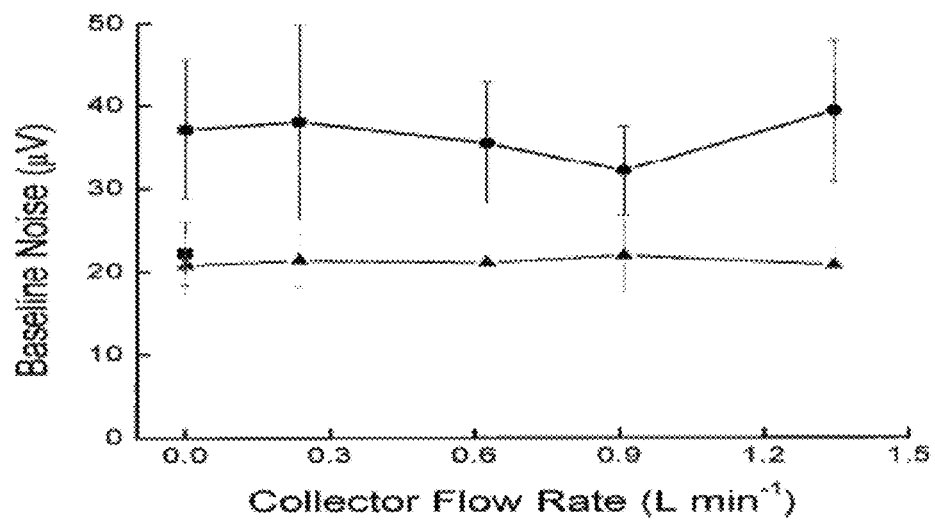
FIG. 8 shows RMS noise measured as a function of growth tube flow rate for the following operating configurations: offline, online without collector grounding, and online with grounding.

Coupling the microchip to the growth tube provides a unique microchip operating environment. Online and offline performance were compared before attempting ambient sampling. Baseline noise measurements were made both offline and online at a variety of growth tube flow rates (using filtered air). FIG. 8 shows RMS noise measured as a function of growth tube flow rate for the following operating configurations: offline (802), online without collector grounding (804), and online with grounding (808). Although flow rate does not significantly affect baseline noise, online performance does suffer from higher noise unless the growth tube outlet metal is grounded. After grounding, online noise levels are equal to or lower than offline values. Noise measurements were acquired from the standard deviation of the baseline in 10-s windows; n=30 for offline mode and n=17-21 for each online measurement.

Functionality of the air duct network for pressure equilibration was tested for the interface configuration of FIG. 2*a*. This was done by analyzing an aqueous mixture of 15-µM analytes in three modes of operation: offline, online with airtight reservoir lids, and online without lids. No discernible differences were seen for the offline and online measurements with reservoir lids, as shown in FIG. 9.

Figure 9:
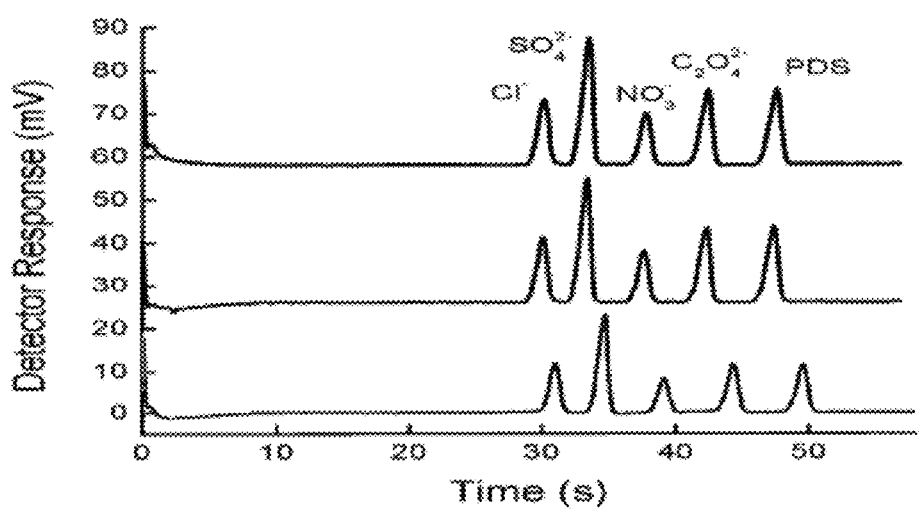
FIG. 9 compares electropherograms obtained for offline operation and when coupled to the growth tube collector.

FIG. 9 compares electropherograms obtained for offline operation and when coupled to the growth tube collector-Without application of the lids, migration times increase and peak areas decrease, especially for later-migrating species. Online percent recovery measurements (defined by the measured online/offline concentration ratios) for chloride, sulfate, nitrate, and oxalate were determined using a single offline calibration curve. Values of 98.7±5.0%, 100.0±0.7%, 100.2±2.3%, and 99.8±0.6% (n=5) were obtained, respectively, confirming isobaric operation and the equivalence of offline and online modes when using reservoir lids. In contrast, respective recoveries without lids were 118.7%, 118.2%, 112.9%, and 104.7% due to altered injection biasing from unwanted hydrodynamic flow. When using the configuration of FIG. 2b the air ducts are not necessary, as the equalization of the pressures is provided by the box.

From the laboratory tests, sensitivities of 1.00, 2.11, 0.84, and 1.28 mVµM$^{-1}$ were obtained for chloride, sulfate, nitrate, and oxalate, respectively, corresponding to aqueous limits of detection of 63, 30, 75, and 50 nM in grounded online mode. These detection limits are 3-4 times lower than previously-published results for this separation. The improvement is attributed to the CD20 analog output offset functionality and improved electronic shielding. These LODs are the best reported to date with these analytes using microchip capillary electrophoresis without stacking and are roughly twenty times better than reported for contactless conductivity detection. With a 1 L min$^{-1}$ collection rate and 30-µL sample volume, aerosol detection limits are estimated at 67, 86, 140, and 131 ng m$^{-3}$ min, respectively. For a 15-min sampling time, respective detection limits are predicted to be 4, 6, 9, and 9 ng m$^{-3}$. The actual LOD in differential analyses is dependent on injection-to-injection precision, and this value was not measured. LODs can be lowered by increasing sampling times, lowering sample volume, or using a low-conductivity sample matrix to enable electrophoretic stacking. For instance, in the development of the separation chemistry, LODs were lowered by a factor of nine by using a sample matrix of 10% background electrolyte (BGE) This approach may not be as effective as desired if the collected aerosols significantly increase the matrix conductivity.

Figure 10A:
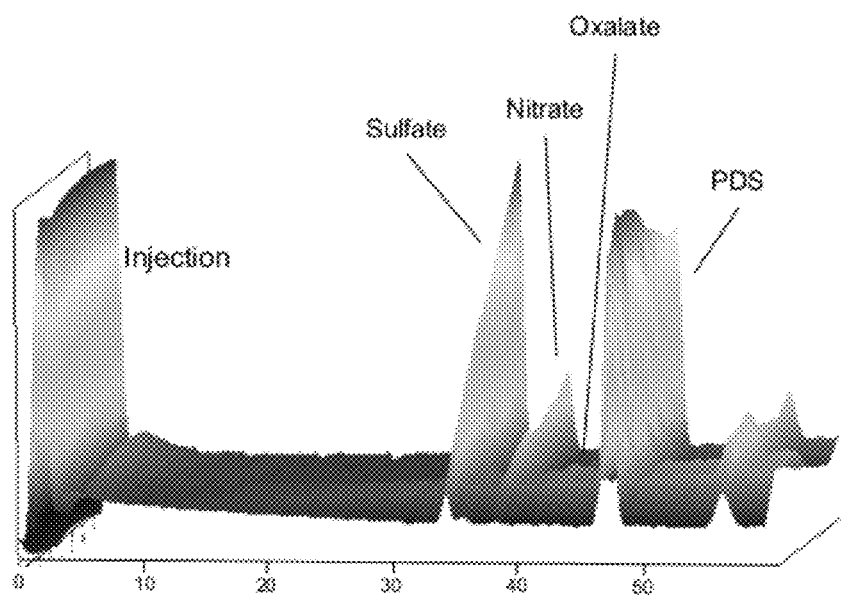
FIGS. 10A and 10B are alternative views of the same graph showing electropherograms from an ambient analysis during one accumulation event.
Figure 10B:
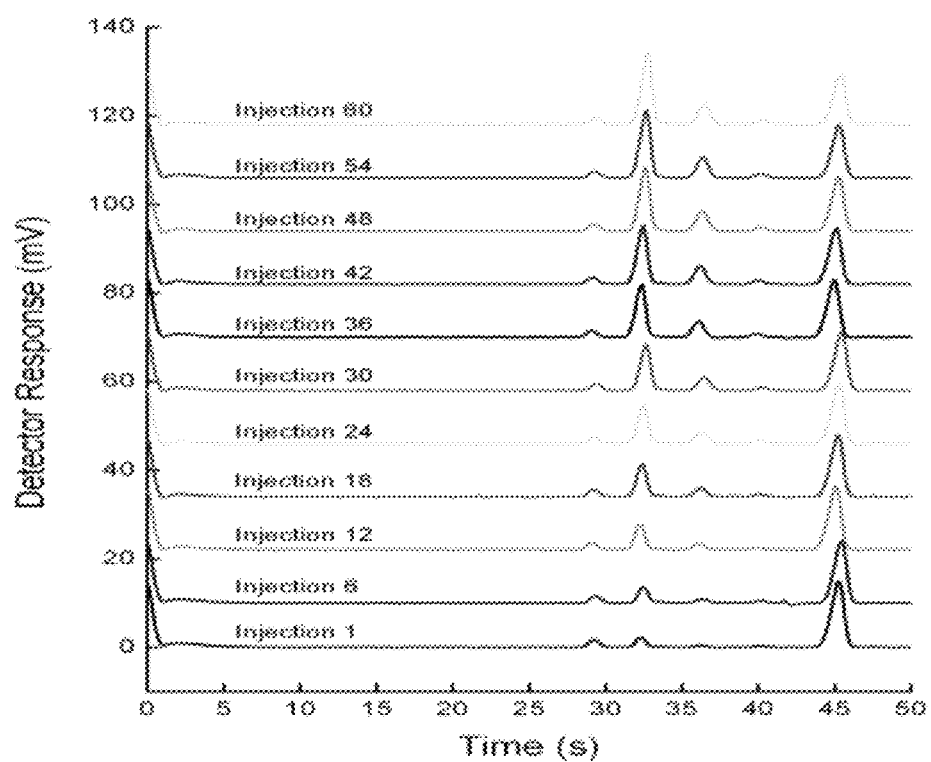

FIGS. 10A and 10B are alternative views of the same graph showing electropherograms from an ambient analysis during one accumulation event. Accumulation of sulfate, nitrate, and oxalate are all evident.

The second and third peaks are sulfate and nitrate, and are clearly increasing with subsequent injections, an effect due to collection of additional sulfate and nitrate aerosol in the sample reservoir. A small amount of oxalate is observed as the fourth peak. The final peak is the internal standard, for which the height decreases slightly due to ion depletion and electrophoretic de-stacking. The analyte migration times were consistent over 24 hours of ambient measurements, with standard deviations of 0.94% for chloride (n=1179), 1.04% for sulfate (1370), 1.01% for nitrate (1249), 0.88% for oxalate (854), and 1.09% for PDS (n=1371). The ambient measurements illustrate that the present technology can provide an alternative for real-time, semi-continuous monitoring of aerosol composition, and the high sensitivity and short analysis times are encouraging. Estimated detection limits for the system are 70-140 ng m$^{-3}$ min for inorganic anions when collecting into 30 µL of solution at 1 L min$^{-1}$.

Another embodiment of the technology uses a microchip with a larger buffer reservoir, a smaller sample reservoir, and smaller microfluidic channels. This has improved detection limits and run time longevity. The volumes of the buffer and waster reservoirs 170, 161 and 171 have been increased from 125 µL to as much as 1500 µL. Separation channel dimensions were decreased to about 1000 µm$^2$ from the original 1400 µm$^2$. The smaller channels and larger buffer volumes both increase uninterrupted operation time. With the original design continuous operation (prior to flushing) was limited to 3 hours. With the improved method this maximum time has increased to over 80 hours, while requiring just 4.5 mL of buffer. It should be noted that the smaller separation channel results in a roughly proportional drop in sensitivity, but improvements in the detection configuration have mostly counteracted this drawback, and current aerosol detection limits have actually improved because the sample reservoir volume was decreased to 21 µL from the previous 30 µL. The smaller sample reservoir would have led to faster sample depletion, but this was avoided by designing a novel system where the sample channel had only half the cross-sectional area of the rest of the microfluidic network. The small sample channel has the additional benefit of increased dampening of any hydrodynamic pulses induced by particle impaction on the sample reservoir surface.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system for sampling aerosol composition, comprising a laminar flow water condensation particle tube;
   an analytical microchip having a sample reservoir and at least one buffer fluid reservoir, and further including a fluid transport control system moving fluid between the respective reservoirs, and a pressure equalization system for the reservoirs; and
   an acceleration nozzle provided at one end of the tube adjacent to the sample reservoir.

2. The system of claim 1 further including a controller and an air pump, the air pump coupled to an exit port to draw air through the acceleration nozzle, and where the ratio of the diameter of the acceleration nozzle ($D_{jet}$) to the two-thirds power of the volumetric air flow through the nozzle ($Q^{2/3}$ mm L$^{-2/3}$ min$^{2/3}$) is between 1 and 2 mm min$^{2/3}$ L$^{-2/3}$.

3. The system of claim 2 wherein a ratio of the square of the diameter of droplet exiting the condensation tube ($D_p^2$) to the flow rate (Q µm$^2$minL$^{-1}$) is more than about 9.

4. The system of claim 1 further including a plurality of acceleration nozzles for the sample reservoir.

5. The system of claim 1 further including a plurality of acceleration nozzles each associated with one of a plurality of sample reservoirs.

6. The system of claim 1 wherein the pressure equalization system comprises at least one lid and a network of air channels incorporated into the microchip.

7. The system of claim 1 wherein the pressure equalization system includes a sealed housing surrounding the acceleration nozzle at one end of the tube.

8. The system of claim 1 further including a flushing system including an inlet line and an outlet line coupled to the sample reservoir.

9. The system of claim 1 further including a controller coupled to the tube and microchip, the controller providing continuous, automated test cycling.

10. The system of claim 1 wherein the fluid transport control system comprises a plurality of electrodes positioned in the reservoirs and a series of flow channels coupling the reservoirs, the fluid moving in the channels and reservoirs under electrokinetic influence.

11. The system of claim 1 wherein the fluid transport system comprises a series of flow channels coupling the reservoirs and the fluid is moved through the channels under hydrodynamic control.

12. A method for sampling aerosols, comprising;
coupling a laminar flow water condensation particle tube having an acceleration nozzle at one end to a sample reservoir in a microchip, the microchip including at least at least one buffer fluid reservoir, a fluid transport control system moving fluid between the respective reservoirs, and a pressure equalization system for the reservoirs;
drawing sample aerosol into the tube to provide sample particles in the sample reservoir;
measuring the sample in the reservoir for a first time period;
ending the measuring and flushing the sample reservoir over a second time period.

13. The method of claim 12 wherein the drawing, measuring, ending and flushing steps are repeated cyclically.

14. The method of claim 12 wherein the step of drawing includes engaging a pump at a housing outlet to withdraw air from the housing thereby pulling air into an inlet an end of the tube and through the accelerator.

15. The method of claim 12 wherein the drawing, measuring, ending and flushing steps are performed by an automated controller.

16. The method of claim 12 wherein a ratio of the diameter of the acceleration nozzle ($D_{jet}$) to the two-thirds power of the volumetric air flow through the nozzle ($Q^{2/3}$ mm $L^{-2/3}$ min$^{2/3}$) is between 1 and 2 mm min$^{2/3}$ $L^{-2/3}$.

17. The method of claim 12 wherein a ratio wherein a ratio of the square of the diameter of droplet exiting the condensation tube ($D_p^2$) to the flow rate ($Q$ $\mu^2$minL$^{-1}$) is more than about 9 L min$^{-1}$ $\mu$m$^{-2}$.

18. An apparatus for sampling aerosol compositions, comprising:
a laminar flow water condensation particle tube having wetted walls and an acceleration nozzle;
an analytical microchip including:
a sample reservoir provided at an interface with the acceleration nozzle;
at least one buffer fluid reservoir;
a fluid transport system moving fluid between the respective reservoirs;
a pressure equalization system for the reservoirs;
one or more electrodes positioned in the reservoirs;
at least two flushing ports in the sample reservoir;
an air pump coupled to the interface;
a flushing pump coupled said ports; and
a controller coupled to the fluid transport system, air ports, and flushing pump.

19. The apparatus of claim 18 wherein the fluid transport system comprises a series of flow channels coupling the reservoirs and the fluid is moved through the channels using an electrokinetic system including a plurality of electrodes in the reservoirs coupled to the controller.

20. The apparatus of claim 19 wherein the acceleration nozzle is made of an electrically non-conducting material.

21. The apparatus of claim 18 wherein the acceleration nozzle is made of an electrically non-conducting material.

* * * * *